(12) United States Patent
Horn et al.

(10) Patent No.: US 11,650,275 B2
(45) Date of Patent: May 16, 2023

(54) MAGNETIC RESONANCE SYSTEM WITH A MAGNETIC RESONANCE DEVICE AND A MAGNETIC RESONANCE-COMPATIBLE ELECTRIC MOTOR

(71) Applicant: Siemens Healthcare GmbH, Erlangen (DE)

(72) Inventors: Christopher Horn, Erlangen (DE); Johann Sukkau, Herzogenaurach (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 17/470,042

(22) Filed: Sep. 9, 2021

(65) Prior Publication Data
US 2022/0075016 A1    Mar. 10, 2022

(30) Foreign Application Priority Data

Sep. 9, 2020 (DE) .......................... 102020211326.2

(51) Int. Cl.
  *G01R 33/54* (2006.01)
  *A61B 5/055* (2006.01)
  *G01R 33/385* (2006.01)

(52) U.S. Cl.
  CPC ............ *G01R 33/543* (2013.01); *A61B 5/055* (2013.01); *G01R 33/385* (2013.01)

(58) Field of Classification Search
  CPC .... G01R 33/543; G01R 33/385; G01R 33/28; A61B 5/055; H02K 7/14; H02K 37/00
  See application file for complete search history.

(56) References Cited

U.S. PATENT DOCUMENTS

| 5,841,278 A | * | 11/1998 | Green | ................ | G01R 33/3657 |
| | | | | | 324/318 |
| 10,330,754 B2 | | 6/2019 | Garcia et al. | | |
| 2010/0264918 A1 | | 10/2010 | Roeck et al. | | |
| 2018/0188340 A1 | * | 7/2018 | Garcia | ................. | H02K 11/215 |
| 2021/0252213 A1 | * | 8/2021 | Nijsse | ................. | A61M 5/1458 |

FOREIGN PATENT DOCUMENTS

| DE | 102008034685 A1 | 10/2009 |
| DE | 102015201044 A1 | 7/2016 |
| DE | 102017131317 A1 | 7/2018 |
| WO | 2016116284 A1 | 7/2016 |

OTHER PUBLICATIONS

Roeck et al., "A variable torque motor compatible with magnetic resonance imaging," Review of Scientific Instruments, 80, 046108 pp. 1-3 (2009).
European Search Report for Application No. 10 2020 211 326.2 dated Sep. 21, 2020.

* cited by examiner

*Primary Examiner* — G. M. A Hyder
(74) *Attorney, Agent, or Firm* — Banner & Witcoff Ltd.

(57) ABSTRACT

A magnetic resonance (MR) system may include a MR device and a MR-compatible drive. The MR device may include a scanner with a basic magnet for generating a homogeneous basic magnetic field. The MR-compatible drive may include an electric motor with a stator. The stator of the electric motor may include a dominant component of the basic magnetic field of the basic magnet.

17 Claims, 6 Drawing Sheets

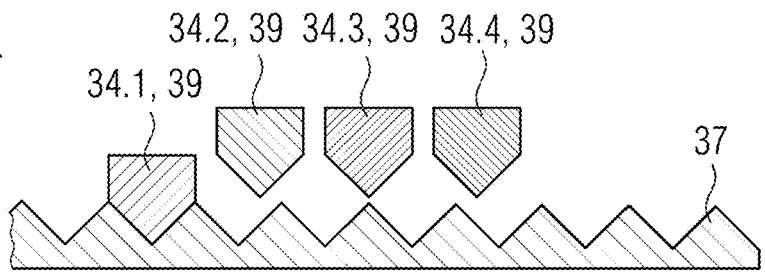
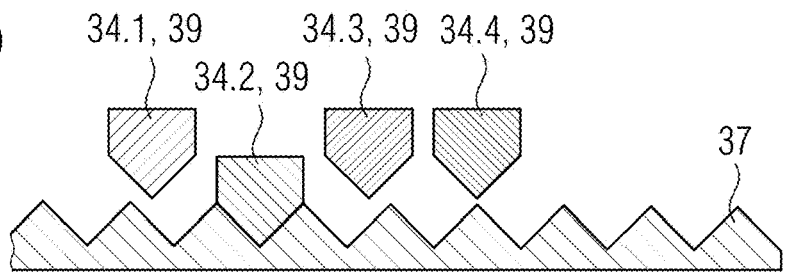
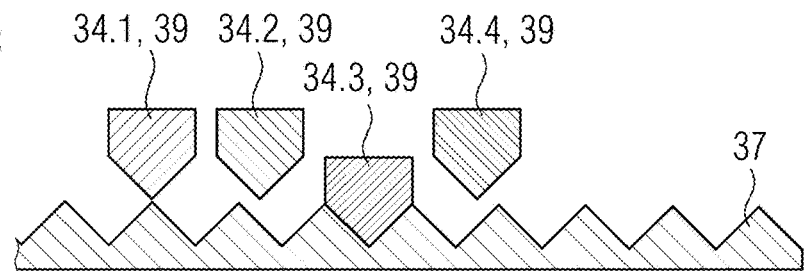
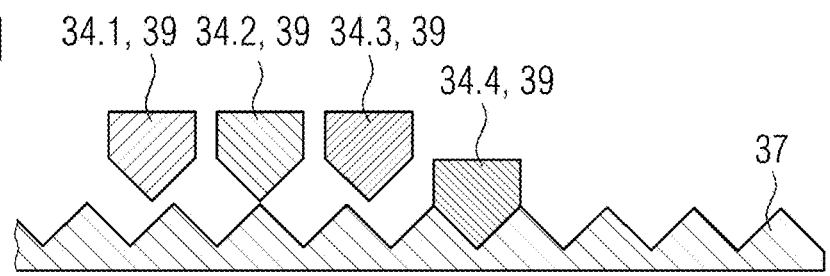
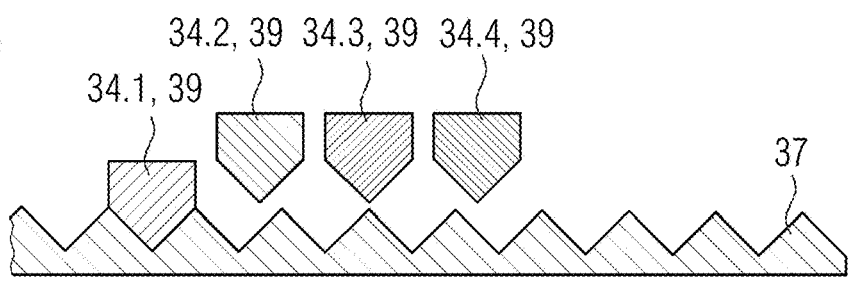

MAGNETIC RESONANCE SYSTEM WITH A MAGNETIC RESONANCE DEVICE AND A MAGNETIC RESONANCE-COMPATIBLE ELECTRIC MOTOR

CROSS REFERENCE TO RELATED APPLICATIONS

This patent application claims priority to German Patent Application No. 10 2020 211 326.2, filed Sep. 9, 2020, which is incorporated herein by reference in its entirety.

BACKGROUND

Field

The present disclosure relates to a magnetic resonance (MR) system with a magnetic resonance device, which comprises a scanner with a basic magnet for generating a homogeneous basic magnetic field, and to a magnetic resonance-compatible drive.

Related Art

In order to monitor robot-assisted interventions on a patient, interventions of this kind are frequently monitored by means of medical imaging. Here medical magnetic resonance devices are also used for monitoring an intervention on a patient. For monitoring of this kind it is a prerequisite, however, that the robot-assisted intervention occurs by means of a magnetic resonance-compatible intervention unit in order to prevent undesirable interactions between the intervention unit and the magnetic resonance measurement and/or the magnetic resonance device. A magnetic resonance-compatible intervention unit of this kind comprises, in particular, a magnetic resonance-compatible drive.

Previous magnetic resonance-compatible drives are designed, in particular, to be pneumatic. However, this also demands the prerequisite that there is compressed air available for the intervention unit. In addition, a pneumatic drive is relatively expensive owing to the design with valves. A further drawback of a pneumatically designed drive is that the pneumatic drive is limited in terms of its speed. The reason for this is that compressed air valves of the pneumatic drive are electromagnetic and are arranged outside of an examination space in which a scanner of the magnetic resonance device is arranged, therefore. This causes a delay between a controller and a motor owing to a build-up of pressure throughout the system.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

FIGS. 6a-6e show a clocking of the magnetic resonance-compatible drive according to an exemplary embodiment.

Figure 1:
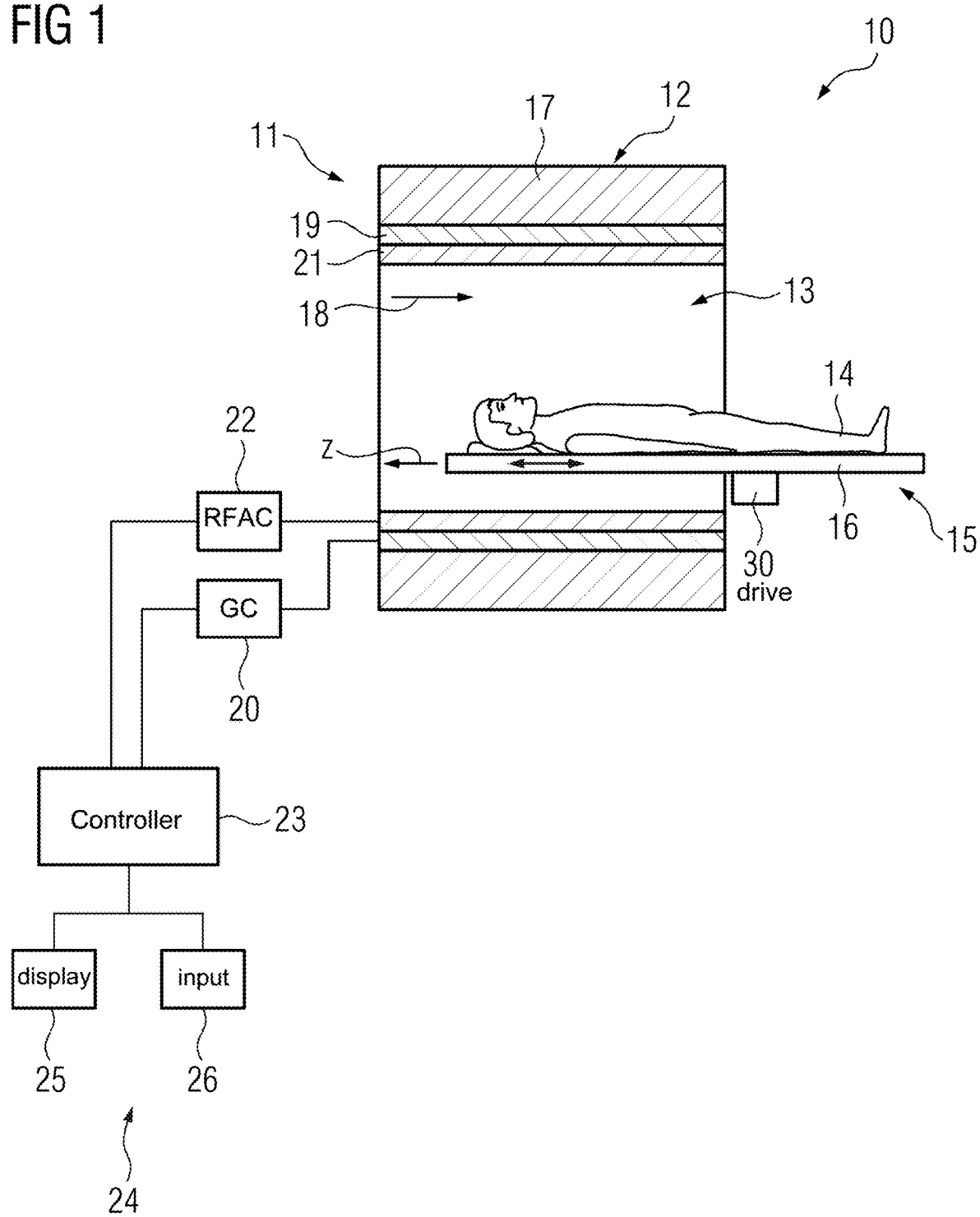
FIG. 1 shows a magnetic resonance system with a magnetic resonance device and a magnetic resonance-compatible drive in a schematic representation, according to an exemplary embodiment.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure. The connections shown in the figures between functional units or other elements can also be implemented as indirect connections, wherein a connection can be wireless or wired. Functional units can be implemented as hardware, software or a combination of hardware and software.

An object of the disclosure is to provide an inexpensive and simply constructed magnetic resonance-compatible drive for a magnetic resonance system.

The disclosure starts from a magnetic resonance system with a magnetic resonance device, which comprises a scanner with a basic magnet for generating a homogeneous basic magnetic field, and a magnetic resonance-compatible drive. The magnetic resonance-compatible drive inventively comprises an electric motor with a stator, wherein the stator of the electric motor comprises a dominant component of the basic magnetic field of the basic magnet.

The magnetic resonance device preferably comprises a medical and/or diagnostic magnetic resonance device, which is configured and/or designed for acquiring medical and/or diagnostic image data, in particular medical and/or diagnostic magnetic resonance image data, of a patient. The scanner of the magnetic resonance device comprises a detector, in particular a magnetic unit, for acquisition of the medical and/or diagnostic image data. In an exemplary embodiment, the scanner, in particular the magnetic unit, comprises the basic magnet, a gradient coil unit and a radio frequency antenna unit.

The basic magnet is designed for generation of a homogeneous basic magnetic field. In particular, the basic magnet is designed for generation of a strong and constant basic magnetic field. The homogeneous basic magnetic field is preferably arranged and/or located within a patient receiving region of the magnetic resonance device. The patient receiving region is configured and/or designed for receiving the patient, in particular of the region of the patient to be examined, for a medical magnetic resonance examination. For example, the patient receiving region has a cylindrical design for this purpose and/or is cylindrically surrounded by the scanner, in particular the magnetic unit.

A Field of View (FOV) and/or an isocenter of the magnetic resonance device is preferably arranged inside the patient receiving region. The FOV preferably comprises an acquisition region of the magnetic resonance device, within which the conditions for an acquisition of medical image data, in particular magnetic resonance image data, exist within the patient receiving region, such as an homogeneous basic magnetic field. The isocenter of the magnetic resonance device preferably comprises the region and/or point inside the magnetic resonance device, which has the optimum and/or most ideal conditions for the acquisition of medical image data. In particular, the isocenter comprises the most homogeneous magnetic field region inside the magnetic resonance device.

Within the patient receiving region and/or close to the isocenter the basic magnetic field of the basic magnet comprises only one dominant component Bo in the z-direction of the magnetic resonance device. The dominant component of the basic magnetic field and/or a scatter field is preferably oriented in the z-direction of the magnetic resonance device outside of the FoV and/or outside of the patient receiving region as well. This dominant component of the basic magnetic field serves as a stator for the magnetic resonance-compatible drive, in particular the electric motor. In an exemplary embodiment, the dominant component of the basic magnetic field is oriented vertically to a motor shaft of the electric motor.

The magnetic resonance system comprises the magnetic resonance-compatible drive, in particular the electric motor. The magnetic resonance-compatible drive, in particular the electric motor, can be used for example for a robot-assisted intervention and/or for calibration tasks. Here a magnetic resonance-compatible drive should be taken to mean, in particular, a drive for use with a magnetic resonance device, wherein the drive is not designed for imaging. In particular, the magnetic resonance-compatible drive does not have any components designed for imaging, so impairment of a magnetic resonance measurement can advantageously be avoided.

The electric motor preferably comprises an electric step motor. The electric step motor preferably comprises the stator and a rotor, in particular a rotatable motor element. The stator comprises the dominant component of the basic magnetic field and/or a scatter field of the basic magnet. The component of the basic magnetic field that acts as a stator, in particular the dominant component of the basic magnetic field, is preferably oriented vertically to a motor shaft of the electric motor here.

The disclosure can advantageously provide a structurally simple and compact drive, in particular magnetic resonance-compatible drive, which can be used together with a magnetic resonance device. Furthermore, an inexpensive and component-saving drive, in particular magnetic resonance-compatible drive, can be provided owing to a simple construction of the drive, in particular of the magnetic resonance-compatible drive. In particular, an electric motor, in particular an electric step motor, without brushes can be provided in this way.

In an advantageous development of the magnetic resonance system it can be provided that the magnetic resonance-compatible drive, in particular the electric motor, has a rotatable motor element with at least one rotatably mounted coil element and a coil axis oriented vertically to the dominant component of the basic magnetic field of the basic magnet, wherein the at least one rotatably mounted coil element is rotatably mounted around the coil axis oriented vertically to the dominant component of the basic magnetic field of the basic magnet.

The rotatable motor element preferably comprises a rotatably mounted and/or a pivotally mounted motor element for generation of a drive moment of the electric motor, in particular of the electric step motor. This rotatable and/or rotating motor element, in particular the rotatably mounted and/or pivotally mounted motor element, is designed as a rotatably mounted coil element. The at least one rotatably mounted coil element is rotatably mounted on the coil axis of the electric motor. A rotary movement of the rotatably mounted and/or pivotally mounted motor element, in particular of the rotatably mounted coil element, can also comprise only a partial rotation and not a complete rotation about the motor shaft. In an exemplary embodiment, the at least one rotatably mounted coil element is mounted to rotate in both directions about the coil axis. The at least one rotatably mounted coil element comprises at least one coil winding or also a plurality of coil windings, wherein the at least one coil winding and/or the plurality of coil windings delimit a coil surface of the at least one rotatably mounted coil element. In an exemplary embodiment, the at least one rotatably mounted coil element has a plurality of windings, so a large force, in particular a large Lorentz force, can act on the at least one rotatably mounted coil element for generation of a drive moment. In an exemplary embodiment, the at least one coil winding comprises a copper wire. On a rotation of the at least one rotatably mounted coil element about the coil axis an inclination of the coil surface changes in respect of the basic magnetic field and/or the dominant component of the basic magnetic field of the basic magnet.

A simple force transfer to the at least one rotatably mounted coil element on a flow of current through the at least one rotatably mounted coil element can be achieved here and a rotation of the at least one rotatably mounted coil element can also be triggered thereby. This is accompanied by a drive moment of the magnetic resonance-compatible drive, in particular of the electric step motor, also being able to be generated particularly easily by way of accompaniment.

In an advantageous development of the magnetic resonance system it can be provided that for generation of a drive moment the at least one rotatably mounted coil element performs a rotary movement, wherein the rotary movement comprises a rotation of the at least one rotatably mounted coil element by at least 5° up to a maximum of 90° about the coil axis. In an exemplary embodiment, the rotary movement comprises a rotation of the at least one rotatably mounted coil element of at least 5° up to a maximum of 80° about the coil axis. In an exemplary embodiment, the rotary movement comprises a rotation of the at least one rotatably mounted coil element of at least 5° up to a maximum of 70° about the coil axis. In an exemplary embodiment, the rotary movement comprises a rotation of the at least one rotatably mounted coil element of at least 5° up to a maximum of 60° about the coil axis. In an exemplary embodiment, the rotary movement comprises a rotation of the at least one rotatably mounted coil element of at least 5° up to a maximum of 50° about the coil axis. In an exemplary embodiment, the rotary movement comprises a rotation of the at least one rotatably mounted coil element of at least 5° up to a maximum of 40° about the coil axis. In an exemplary embodiment, the rotary movement comprises a rotation of the at least one rotatably mounted coil element of at least 5° up to a maximum of 30° about the coil axis. In an exemplary embodiment, the rotary movement comprises a rotation of the at least one rotatably mounted coil element of at least 8° up to a maximum of 25° about the coil axis. In an exemplary embodiment, the rotary movement comprises a rotation of the at least one rotatably mounted coil element of at least 10° up to a maximum of 22° about the coil axis. In an exemplary embodiment, the rotary movement comprises a rotation of the at least one rotatably mounted coil element of at least 10° up to a maximum of 20° about the coil axis.

In an exemplary embodiment, a coil surface of the at least one rotatably mounted coil element changes an inclination in respect of a direction of the basic magnetic field and/or of the dominant component of the basic magnetic field of the basic magnet by at least 5° up to a maximum of 90°. Particularly advantageously, the coil surface of the at least one rotatably mounted coil element changes an inclination in respect of the direction of the basic magnetic field and/or the dominant component of the basic magnetic field of the basic magnet by at least 5° up to a maximum of 80°. Particularly advantageously, the coil surface of the at least one rotatably mounted coil element changes an inclination in respect of the direction of the basic magnetic field and/or the dominant component of the basic magnetic field of the basic magnet by at least 5° up to a maximum of 70°. Particularly advantageously, the coil surface of the at least one rotatably mounted coil element changes an inclination in respect of the direction of the basic magnetic field and/or the dominant component of the basic magnetic field of the basic magnet by at least 5° up to a maximum of 60°. Particularly advantageously, the coil surface of the at least one rotatably mounted coil element changes an inclination in respect of the direction of the basic magnetic field and/or the dominant component of the basic magnetic field of the basic magnet by at least 5° up to a maximum of 50°. Particularly advantageously, the coil surface of the at least one rotatably mounted coil element changes an inclination in respect of the direction of the basic magnetic field and/or the dominant component of the basic magnetic field of the basic magnet by at least 5° up to a maximum of 40°. Particularly advantageously, the coil surface of the at least one rotatably mounted coil element changes an inclination in respect of the direction of the basic magnetic field and/or the dominant component of the basic magnetic field of the basic magnet by at least 5° up to a maximum of 30°. Particularly advantageously, the coil surface of the at least one rotatably mounted coil element changes an inclination in respect of the direction of the basic magnetic field and/or the dominant component of the basic magnetic field of the basic magnet by at least 8° up to a maximum of 25°. Particularly advantageously, the coil surface of the at least one rotatably mounted coil element changes an inclination in respect of the direction of the basic magnetic field and/or the dominant component of the basic magnetic field of the basic magnet by at least 10° up to a maximum of 22°. Particularly advantageously, the coil surface of the at least one rotatably mounted coil element changes an inclination in respect of the direction of the basic magnetic field and/or the dominant component of the basic magnetic field of the basic magnet by at least 10° up to a maximum of 20°.

A particularly compact drive, in particular a particularly compact electric step motor, can be provided owing to the small angle of rotation of the at least one rotatably mounted coil element. A further advantage is that, owing to the small angle of rotation of the at least one rotatably mounted coil element, it is possible to utilize a flexibility of wires and rotatable current transfers, such as, in particular, by means of brushes and/or sliding contacts, can advantageously be omitted, therefore.

In an advantageous development of the magnetic resonance system it can be provided that when a voltage is applied to the at least one rotatably mounted coil element, a rotary movement is triggered at the at least one rotatably mounted coil element. In particular, when a preferably defined voltage is applied, a flow of current is generated through the at least one rotatably mounted coil element. This is accompanied by the generation of a Lorentz force, which acts on the at least one rotatably mounted coil element, wherein the Lorentz force causes a rotary movement and/or a tilting movement of the at least one rotatably mounted coil element. A direction of the rotary movement and/or the tilting movement due to a current direction of a flow of current through the at least one rotatably mounted coil element and/or due to a direction of a voltage applied to the at least one rotatably mounted coil element can be established in the process.

In an advantageous development of the magnetic resonance system it can be provided that the magnetic resonance-compatible drive, in particular the electric motor, has at least one stop element. In an exemplary embodiment, the magnetic resonance-compatible drive, in particular the electric step motor, has two stop elements for limitation of a rotary movement of the at least one rotatably mounted coil element, so a rotary movement of the at least one rotatably mounted coil element can be limited in any direction about the coil axis. In an exemplary embodiment, the at least one stop element comprises an elastic stop element and/or a damping stop element, in particular a stop element made from an elastic and/or damping material. In an exemplary embodiment, the magnetic resonance-compatible drive, in particular the electric motor, has one stop element, preferably two stop elements, for each rotatably mounted coil element so a rotary movement for each rotatably mounted coil element of the magnetic resonance-compatible drive, in particular of the electric motor, can advantageously be limited.

In an advantageous development of the magnetic resonance system it can be provided that the at least one rotatably mounted coil element has a positive-fitting transfer element for transfer of a drive moment to a drive shaft of the magnetic resonance-compatible drive, in particular of the electric motor. In this way, a drive moment generated by means of the at least one rotatably mounted coil element can be transferred particularly easily to the drive shaft. In an exemplary embodiment, the drive shaft has a transfer element, in particular positive-fitting transfer element, corresponding to the positive-fitting transfer element of the at least one rotatably mounted coil element for this.

Particularly advantageously, the positive-fitting transfer element of the at least one rotatably mounted coil element comprises a pinion here. In addition, the positive-fitting transfer element of the drive shaft also comprises a toothed wheel, which is designed to be compatible with the pinion of the at least one rotatably mounted coil element. In an exemplary embodiment, the positive-fitting transfer element, in particular the pinion, of the at least one rotatably mounted coil element, on a rotation about the coil axis and/or in a defined tilt position, transfers a drive moment to the positive-fitting transfer element, in particular the toothed wheel, of the drive shaft. The pinion can have a toothing only in a region which comes into contact with the positive-fitting transfer element, in particular the toothed wheel, of the drive shaft.

In an advantageous development of the magnetic resonance system it can be provided that the magnetic resonance-compatible drive has a controller for an actuation of the at least one rotatably mounted coil element.

The inventive controller comprises at least one arithmetic module and/or a processor, wherein the controller is designed for control of the at least one rotatably mounted coil element. In particular, the controller is designed for actuation of all rotatably mounted coil elements incorporated by the magnetic resonance-compatible drive, in particular the electric step motor. In particular the controller is thus designed to execute computer-readable instructions in order to actuate the at least one rotatably mounted coil element. The controller can comprise a memory unit, with computer-readable information being stored on the memory unit, with the controller being designed to load the computer-readable information from the memory unit and to execute the computer-readable information in order to perform an actuation of the at least one rotatably mounted coil element. In addition, for actuation of the at least one rotatably mounted coil element, individual components of the controller can be designed in the form of software components. Basically, some of these components of the controller can also be implemented in the form of software-assisted hardware components, for example FPGAs or the like.

This embodiment of the disclosure enables an advantageously coordinated actuation of the at least one rotatably mounted coil element with a drive moment provided by the magnetic resonance-compatible drive. In particular, coordination with a component to be moved inside the magnetic resonance device with the magnetic resonance-compatible drive can advantageously occur. If the magnetic resonance-compatible drive, in particular the electric step motor, has a plurality of rotatably mounted coil elements, advantageous actuation of all rotatably mounted coil element incorporated by the magnetic resonance-compatible drive can be coordinated with each other by means of the controller.

In an advantageous development of the magnetic resonance system it can be provided that the magnetic resonance-compatible drive has at least one switching element for actuation of the at least one rotatably mounted coil element. In an exemplary embodiment, the at least one switching element comprises an electronic switching element. The at least one switching element, in particular the electronic switching element, can comprise, for example, a relay, in particular a solid-state relay. Particularly advantageously, however, the at least one switching element, in particular the electronic switching element, comprises a bridge circuit, also called an H-bridge. The bridge circuit, in particular the H-bridge, can comprise a plurality of transistors, in particular bipolar transistors and/or field effect transistors and/or IGBT transistors. By means of such an H-bridge it is possible to achieve by way of advantageous actuation of the H-bridge a simple pole reversal at the electric motor, in particular at the at least one rotatably mounted coil element, and thereby also particularly easily a change in a direction of rotation of the at least one rotatably mounted coil element. A direction of the rotary movement of the at least one rotatably mounted coil element can advantageously be changed by the pole reversal of the current direction at the at least one rotatably mounted coil element. A further advantage of an H-bridge is that exactly one single H-bridge is sufficient for control of a direction of rotation of a rotatably mounted coil element. By contrast, with an implementation of an actuation of a rotatably mounted coil element with relays, two relays, and therewith also two switching elements, always have to be installed. In addition, a particularly compact and inexpensive magnetic resonance-compatible drive, in particular an inexpensive electric step motor, can be provided.

In an advantageous development of the magnetic resonance system it can be provided that the magnetic resonance-compatible drive, in particular the electric motor, has two or more rotatably mounted coil elements. Particularly advantageously, the rotatable motor element of the magnetic resonance-compatible drive, in particular of the electric step motor, has four rotatably mounted coil elements. In this way it is advantageously possible to provide a clocked electric motor, in particular electric step motor, in which the individual rotatably mounted coil elements perform only slight movements and a compact construction of the electric step motor can be achieved thereby. In an exemplary embodiment, the individual rotatably mounted coil elements perform a rotary movement one after the other for generation of a drive moment.

In an advantageous development of the magnetic resonance system it can be provided that the two or more rotatably mounted coil elements are actuated one after the other for a 4-time clock of the electric motor. In an exemplary embodiment, each clock comprises a rotary movement of one of the two or more rotatably mounted coil elements, wherein the rotary movement of the one of the two or more rotatably mounted coil elements causes a rotation of the transfer element, in particular of the toothed wheel, of the drive shaft about a ¼-step of the transfer element of the drive shaft. If the individual coil elements of the two or more rotatably mounted coil elements are actuated one after the other in such a way that the two or more rotatably mounted coil elements perform four clocks of the electric motor one after the other, then this generates a step at the drive shaft. In an exemplary embodiment, a step of the drive shaft here comprises, in particular, a spacing between two teeth of a toothing of the positive-fitting transfer element, in particular of the toothed wheel, of the drive shaft. For example, a step at the transfer element of the drive shaft, in particular the toothed wheel of the drive shaft, can comprise a rotation about 2° of the toothed wheel and/or the drive shaft. High positional accuracy of the magnetic resonance-compatible drive, in particular of the electric motor, can be achieved in this way.

In an advantageous development of the magnetic resonance system it can be provided that at least two of the two or more rotatably mounted coil elements are rotatably mounted, independently of each other, on a shared coil axis. A particularly compact and component-saving construction of the magnetic resonance-compatible drive, in particular of the electric step motor, can advantageously be achieved in this way.

FIG. 1 schematically illustrates a magnetic resonance system 10 with a magnetic resonance device 11. The magnetic resonance device 11 comprises a scanner 12 formed by a magnetic unit. In addition, the magnetic resonance device 11 has a patient receiving region 13 for receiving a patient 14. The patient receiving region 13 in the present exemplary embodiment is cylindrical and cylindrically surrounded in a circumferential direction by the scanner 12, in particular by the magnetic unit. Basically however, a different design of the patient receiving region 13 is always conceivable. The patient 14 can be pushed and/or moved by means of a patient supporting device 15 of the magnetic resonance device 11 into the patient receiving region 13. For this purpose the patient supporting device 15 has a patient couch 16 designed so it can move inside the patient receiving region 13. In particular, the patient couch 16 is mounted so it can move in the direction of a longitudinal extension of the patient receiving region 13 and/or in the z-direction.

The scanner 12, in particular the magnetic unit, comprises a superconducting basic magnet 17 for generating a strong and, in particular, constant basic magnetic field 18. Furthermore, the scanner 12, in particular the magnetic unit, has a gradient coil 19 for generation of magnetic field gradients, which are used for spatial encoding during imaging. The gradient coil 19 is controlled by means of a gradient controller 20 of the magnetic resonance device 11. The scanner 12, in particular the magnetic unit, also comprises a radio frequency antenna 21 for excitation of a polarization, which is established in the basic magnetic field 18 generated by the basic magnet 17. The radio frequency antenna 21 is controlled by a radio frequency (RF) antenna controller 22 of the magnetic resonance device 11 and irradiates radio frequency magnetic resonance sequences into the patient receiving region 13 of the magnetic resonance device 11. In an exemplary embodiment, one or more components of the magnetic resonance device 11, such as gradient controller 20 and/or the RF antenna controller 22, includes processing circuitry that is configured to perform one or more respective functions and/or operations of the component(s).

The magnetic resonance device 11 may include a system controller 23 configured to control the basic magnet 17, gradient controller 19, and the radio frequency antenna controller 21. The system controller 23 centrally controls the magnetic resonance device 11, for example carrying out a predetermined imaging gradient echo sequence. In addition, the system controller 23 comprises an evaluator (not shown in further detail) for evaluation of medical image data, which is acquired during the magnetic resonance examination. The evaluator may include one or more processors configured to evaluate medical image data. In an exemplary embodiment, the controller 23 includes processing circuitry that is configured to perform one or more functions and/or operations of the controller 23, including controlling the magnetic resonance device 11, processing magnetic resonance signals, reconstructing magnetic resonance images, processing input from the user of the magnetic resonance imaging device 11 and/or providing an output to the user. In this example, one or more components may additionally or alternatively include processing circuitry configured to perform one or more respective functions of the component(s).

Furthermore, the magnetic resonance device 11 comprises a user interface 24, which is connected to the system controller 23. Control information, such as imaging parameters, and reconstructed magnetic resonance images can be displayed on a display 25, for example on at least one monitor, of the user interface 24 for a medical operator. Furthermore, the user interface 24 has an input 26, by means of which information and/or parameters can be input by the medical operator during a measuring procedure.

The illustrated magnetic resonance device 11 can of course comprise further components, which magnetic resonance devices 11 conventionally have. A general mode of operation of a magnetic resonance device 11 is also known to the person skilled in the art, so a detailed description of the further components will be omitted.

The magnetic resonance system 10 also has a magnetic resonance-compatible drive 30 with an electric motor 31, in particular an electric step motor. The magnetic resonance-compatible drive 30 is configured and/or designed in the present exemplary embodiment for generation of a drive moment for a movement of the patient supporting device 14, in particular of the patient couch 16. The magnetic resonance-compatible drive 30 is arranged outside of the patient receiving region. The magnetic resonance-compatible drive 30 is arranged in a base unit (not shown in further detail) of the patient supporting device 15. The base unit is stationary in respect of the scanner 12. In addition, the base unit is arranged underneath the patient couch 16. In an alternative embodiment of the disclosure the magnetic resonance-compatible drive can also be configured and/or designed for generation of a drive moment for an intervention unit, etc.

Figure 2:
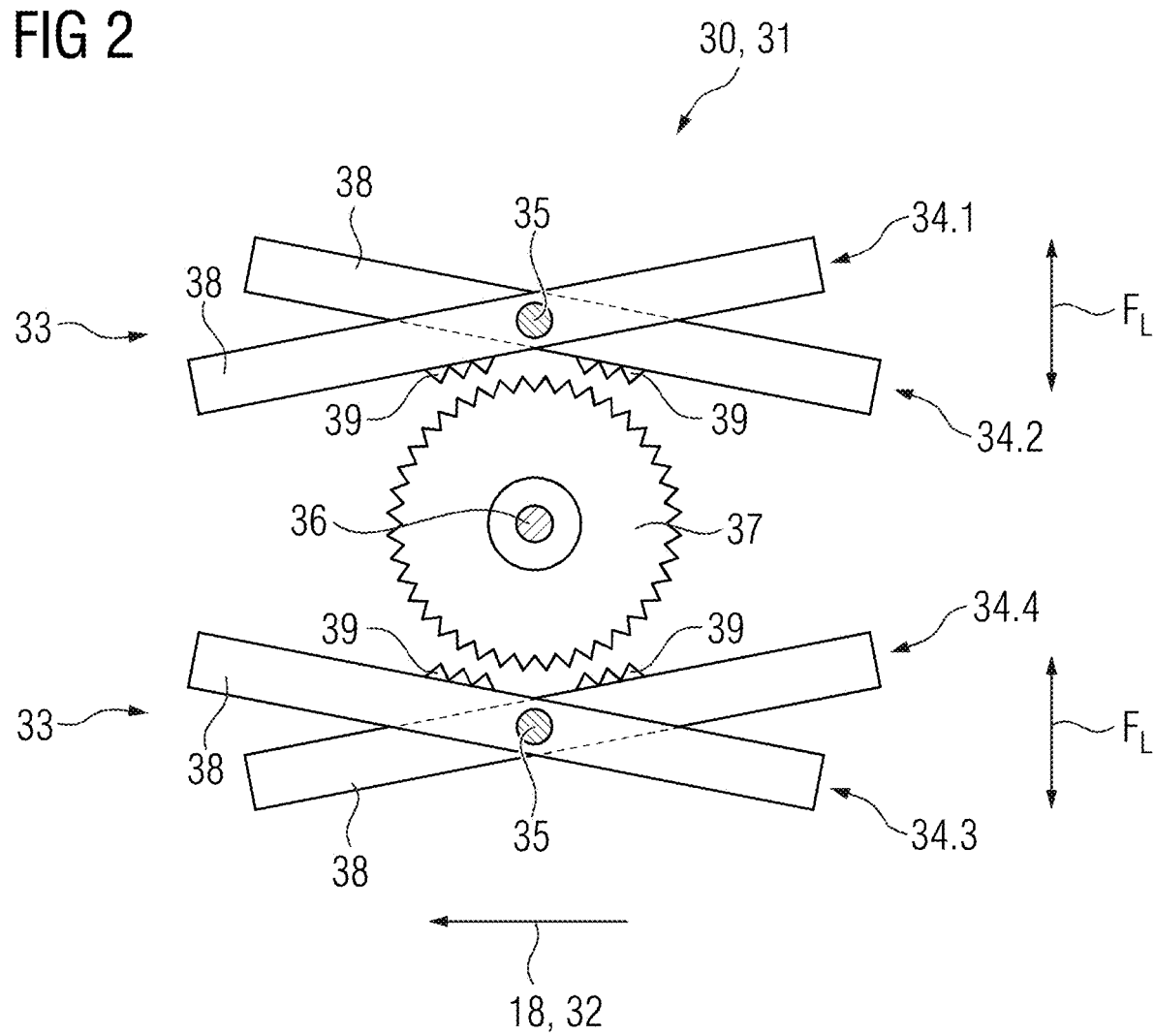
FIG. 2 shows a schematic construction of the magnetic resonance-compatible drive, according to an exemplary embodiment.
Figure 3:
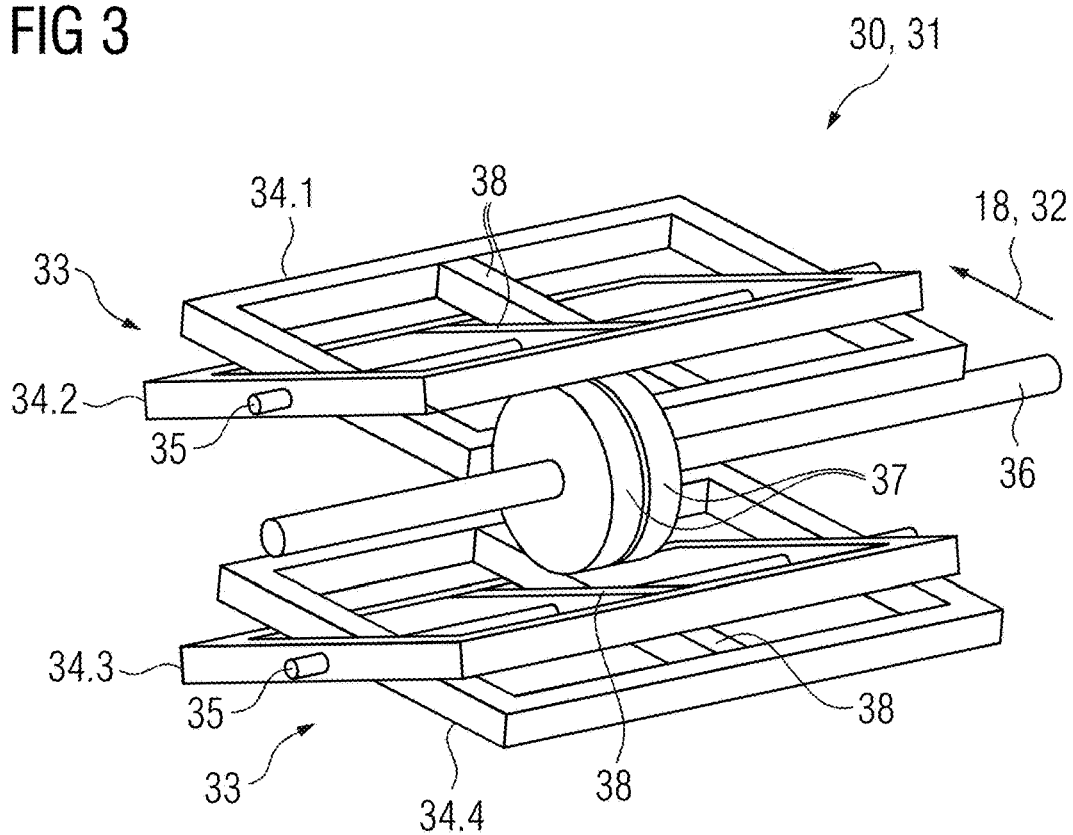
FIG. 3 shows a further view of the magnetic resonance-compatible drive, according to an exemplary embodiment.

FIG. 2 shows the magnetic resonance-compatible drive 30, in particular the electric step motor, in a schematic section, and in a schematic 3D-representation in FIG. 3. The electric step motor of the magnetic resonance-compatible drive 30 comprises a stator 32 and a rotatable motor element 33. The stator 32 of the electric step motor in the present exemplary embodiment comprises a dominant component of the basic magnetic field 18 of the basic magnet 17 in the z-direction of the magnetic resonance device 10. In particular with an arrangement of the magnetic resonance-compatible drive 30 in the isocenter and/or in the vicinity of the isocenter of the magnetic resonance device 11 the stator 32 comprises the dominant component of the basic magnetic field 18 of the magnetic resonance device 11, therefore.

The rotatable motor element 33 of the electric step motor of the magnetic resonance-compatible drive 30 comprises at least one rotatably mounted coil element 34.1, 34.2, 34.3, 34.4. In the present exemplary embodiment, the rotatable motor element 33 of the electric step motor of the magnetic resonance-compatible drive 30 comprises four rotatably mounted coil elements 34.1, 34.2, 34.3, 34.4. The rotatable motor element 33 of the electric step motor of the magnetic resonance-compatible drive 30 also has a plurality of coil axes 35, wherein the rotatably mounted coil elements 34.1, 34.2, 34.3, 34.4 are rotatably mounted on the plurality of coil axes 35. In the present exemplary embodiment, in each case two of the rotatably mounted coil elements 34.1, 34.2, 34.3, 34.4 are rotatably mounted on a shared coil axis 35, with the individual rotatably mounted coil elements 34.1, 34.2, 34.3, 34.4 being mounted to move independently of each other, in particular to rotate, on the respective coil axis 35. The individual coil axes 35 of the rotatable motor element 33 are oriented vertically to the basic magnetic field 18, in particular to the dominant component of the basic magnetic field 18, of the basic magnet 17. In the present exemplary embodiment, the individual rotatably mounted coil elements 34.1, 34.2, 34.3, 34.4 are rotatably mounted in the center of the coil axis 35.

The magnetic resonance-compatible drive 30 also has a drive shaft 36 to which a drive moment is transferred during operation of the magnetic resonance-compatible drive 30, in particular of the electric step motor. For this the drive shaft 36 has a positive-fitting transfer element, which is compatible with one positive-fitting transfer element respectively of the individual rotatably mounted coil elements. In the present exemplary embodiment the positive-fitting transfer element of the drive shaft 36 is incorporated by a toothed wheel 37. In addition, in the present exemplary embodiment the drive shaft 36 has two positive-fitting transfer elements, which are each formed by a toothed wheel 37, FIG. 3. The two toothed wheels 37 of the drive shaft 36 are successively arranged on the drive shaft.

The individual positive-fitting transfer elements of the individual rotatably mounted coil elements 34.1, 34.2, 34.3, 34.4 are incorporated in the present exemplary embodiment by a pinion 38. In addition, further positive-fitting transfer elements that appear expedient to a person skilled in the art are always conceivable between the rotatably mounted coil elements 34.1, 34.2, 34.3, 34.4 and the drive shaft 36 for transfer of a drive moment to the drive shaft 36.

The positive-fitting transfer element, in particular the pinion 38, of the individual rotatably mounted coil elements 34.1, 34.2, 34.3, 34.4 is also oriented vertically to the coil axis 35 and extends transversely through the rotatably mounted coil element 34.1, 34.2, 34.3, 34.4. However, only the section of the pinion 38 making contact with the drive shaft 36, in particular the toothed wheel 37 of the drive shaft, comprises a toothing 39 for transfer of a drive moment to the toothed wheel 37 of the drive shaft 36.

The drive shaft 36 is arranged between the two coil axes 35 for rotatable support of the rotatably mounted coil elements 34.1, 34.2, 34.3, 34.4. Two of the rotatably mounted coil elements 34.1, 34.2, 34.3, 34.4 are arranged on a first side of the drive shaft 36 and the further two rotatably mounted coil elements 34.1, 34.2, 34.3, 34.4 are arranged on a side of the drive shaft 36 opposing the first side, therefore. The two rotatably mounted coil elements 34.1, 34.2, 34.3, 34.4 on the first side of the drive shaft 36 are arranged on the coil axis 35 in such a way that a spacing between the two pinions 38 of the two rotatably arranged coil elements 34.1, 34.2, 34.3, 34.4 corresponds to a spacing of the two toothed wheels 37 on the drive shaft 36. In addition, the two further rotatably mounted coil elements 34.1, 34.2, 34.3, 34.4 are arranged on the side of the drive shaft 36 opposing the first side in such a way that a spacing between the two pinions 38 of the two rotatably arranged coil elements 34.1, 34.2, 34.3, 34.4 corresponds to a spacing of the two toothed wheels 37 on the drive shaft 36. A drive moment can be transferred to each toothed wheel 37 of the drive shaft 36 on each side of the drive shaft 36 by exactly one rotatably mounted coil element 34.1, 34.2, 34.3, 34.4, in particular with exactly one pinion 38, therefore.

The individual rotatably mounted coil elements 34.1, 34.2, 34.3, 34.4 each have a coil winding (not shown in further detail). In an exemplary embodiment, the coil winding in each case comprises a copper wire coil winding for the individual rotatably mounted coil elements 34.1, 34.2, 34.3, 34.4. In an exemplary embodiment, the individual rotatably mounted coil elements 34.1, 34.2, 34.3, 34.4 have a plurality of coil windings here, so a force acting on the rotatably mounted coil elements 34.1, 34.2, 34.3, 34.4 when a voltage is applied to the rotatably mounted coil elements 34.1, 34.2, 34.3, 34.4 is all the greater and the individual rotatably mounted coil elements 34.1, 34.2, 34.3, 34.4 perform a rotary movement, for generation of the drive moment, therefore. The coil winding of the individual rotatably mounted coil elements 34.1, 34.2, 34.3, 34.4 delimit a coil surface of the individual rotatably mounted coil elements 34.1, 34.2, 34.3, 34.4. The pinions 38 of the individual rotatably mounted coil elements 34.1, 34.2, 34.3, 34.4 runs through a central region through the coil surface of the respective rotatably mounted coil elements 34.1, 34.2, 34.3, 34.4.

When a voltage is applied to the individual rotatably mounted coil elements 34.1, 34.2, 34.3, 34.4 a current flows through the individual rotatably mounted coil elements 34.1, 34.2, 34.3, 34.4, so a rotary movement is triggered at the individual rotatably mounted coil elements 34.1, 34.2, 34.3, 34.4. The rotary movement is triggered by a Lorentz force $F_L$ acting on the rotatably mounted coil elements 34.1, 34.2, 34.3, 34.4. The Lorentz force $F_L$ is described by:

$$F_L = I*B*L*2*N$$

Here I is the current strength of a current flowing through the rotatably mounted coil elements 34.1, 34.2, 34.3, 34.4. B comprises the flux density of the basic magnetic field 18, in particular of the dominant component of the basic magnetic field 18. L describes a length of the rotatably mounted coil elements 34.1, 34.2, 34.3, 34.4. N describes the number of coil windings of the individual rotatably mounted coil elements 34.1, 34.2, 34.3, 34.4.

Figure 4:
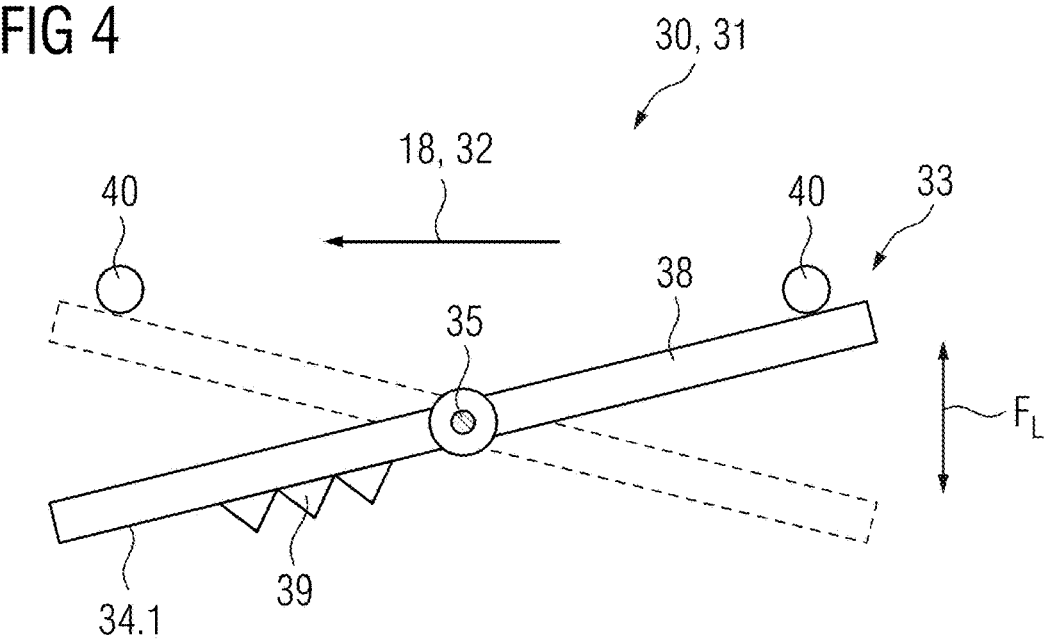
FIG. 4 shows a mode of operation of the magnetic resonance-compatible drive on the basis of a rotatably mounted coil element, according to an exemplary embodiment.

In order to limit a rotary movement of the individual rotatably mounted coil elements 34.1, 34.2, 34.3, 34.4 the magnetic resonance-compatible drive 30, in particular the electric step motor, has at least one stop element 40 for each of the rotatably mounted coil elements 34.1, 34.2, 34.3, 34.4, as is shown in FIG. 4. In the present exemplary embodiment the magnetic resonance-compatible drive 30, in particular the electric step motor, has two stop elements 40 for each of the rotatably mounted coil elements 34.1, 34.2, 34.3, 34.4 in order to limit a rotary movement in both directions of rotation of the rotatably mounted coil element using a single rotatably mounted coil element 34.1, 34.2, 34.3, 34.4, as is shown by way of example in FIG. 4 on the basis of a single rotatably mounted coil element 34.1, 34.2, 34.3, 34.4. The two stop elements 40 have a damping and/or elastic design. The individual stop elements 40 can have a damping and/or elastic form. Alternatively or in addition, the individual stop elements 40 can also comprise a damping and/or elastic material.

The individual stop elements 40 are arranged in respect of the respective rotatably mounted coil element 34.1, 34.2, 34.3, 34.4 in such a way that the rotary movement performed by the rotatably mounted coil elements 34.1, 34.2, 34.3, 34.4 for generation of the drive moment executes a rotation of at least 5° and up to a maximum of 90°. In an exemplary embodiment, the rotary movement comprises a rotation of the individual rotatably mounted coil elements 34.1, 34.2, 34.3, 34.4 of at least 5° up to a maximum of 80° about the coil axis 35. In an exemplary embodiment, the rotary movement comprises a rotation of the individual rotatably mounted coil elements 34.1, 34.2, 34.3, 34.4 of at least 5° up to a maximum of 70° about the coil axis 35. In an exemplary embodiment, the rotary movement comprises a rotation of the individual rotatably mounted coil elements 34.1, 34.2, 34.3, 34.4 of at least 5° up to a maximum of 60° about the coil axis 35. In an exemplary embodiment, the rotary movement comprises a rotation of the individual rotatably mounted coil elements 34.1, 34.2, 34.3, 34.4 of at least 5° up to a maximum of 50° about the coil axis 35. In an exemplary embodiment, the rotary movement comprises a rotation of the individual rotatably mounted coil elements 34.1, 34.2, 34.3, 34.4 of at least 5° up to a maximum of 40° about the coil axis 35. In an exemplary embodiment, the rotary movement comprises a rotation of the individual rotatably mounted coil elements 34.1, 34.2, 34.3, 34.4 of at least 5° up to a maximum of 30° about the coil axis 35. In an exemplary embodiment, the rotary movement of the individual rotatably mounted coil elements 34.1, 34.2, 34.3, 34.4 comprises a rotation of at least 8° up to a maximum of 25° about the coil axis 35. In an exemplary embodiment, the rotary movement of the individual rotatably mounted coil elements 34.1, 34.2, 34.3, 34.4 comprises a rotation of at least 10° up to a maximum of 22° about the coil axis 35. In an exemplary embodiment, the rotary movement of the individual rotatably mounted coil elements 34.1, 34.2, 34.3, 34.4 comprises a rotation of at least 10° up to a maximum of 20° about the coil axis 35.

In an exemplary embodiment, the coil surfaces of the individual rotatably mounted coil elements 34.1, 34.2, 34.3, 34.4 change an inclination in respect of a direction of the basic magnetic field 18 and/or the dominant component of the basic magnetic field 18 of the basic magnet 17 by at least 5° up to a maximum of 90°. Particularly advantageously, the coil surfaces of the individual rotatably mounted coil elements 34.1, 34.2, 34.3, 34.4 change an inclination in respect of the direction of the basic magnetic field 18 and/or the dominant component of the basic magnetic field 18 of the basic magnet 17 by at least 5° up to a maximum of 80°. Particularly advantageously, the coil surfaces of the individual rotatably mounted coil elements 34.1, 34.2, 34.3, 34.4 change an inclination in respect of the direction of the basic magnetic field 18 and/or the dominant component of the basic magnetic field 18 of the basic magnet 17 by at least 5° up to a maximum of 70°. Particularly advantageously, the coil surfaces of the individual rotatably mounted coil elements 34.1, 34.2, 34.3, 34.4 change an inclination in respect of the direction of the basic magnetic field 18 and/or the dominant component of the basic magnetic field 18 of the basic magnet 17 by at least 5° up to a maximum of 60°. Particularly advantageously, the coil surfaces of the individual rotatably mounted coil elements 34.1, 34.2, 34.3, 34.4 change an inclination in respect of the direction of the basic magnetic field 18 and/or the dominant component of the basic magnetic field 18 of the basic magnet 17 by at least 5° up to a maximum of 50°. Particularly advantageously, the coil surfaces of the individual rotatably mounted coil elements 34.1, 34.2, 34.3, 34.4 change an inclination in respect of the direction of the basic magnetic field 18 and/or the dominant component of the basic magnetic field 18 of the basic magnet 17 by at least 5° up to a maximum of 40°. Particularly advantageously, the coil surfaces of the individual rotatably mounted coil elements 34.1, 34.2, 34.3, 34.4 change an inclination in respect of the direction of the basic magnetic field 18 and/or the dominant component of the basic magnetic field 18 of the basic magnet 17 by at least 5° up to a maximum of 30°. Particularly advantageously, the coil surfaces of the individual rotatably mounted coil elements 34.1, 34.2, 34.3, 34.4 change an inclination in respect of the direction of the basic magnetic field 18 and/or the dominant component of the basic magnetic field 18 of the basic magnet 17 by at least 8° up to a maximum of 25°. Particularly advantageously, the coil surfaces of the individual rotatably mounted coil elements 34.1, 34.2, 34.3, 34.4 change an inclination in respect of the direction of the basic magnetic field 18 and/or the dominant component of the basic magnetic field 18 of the basic magnet 17 by at least 10° up to a maximum of 22°. Particularly advantageously, the coil surfaces of the individual rotatably mounted coil elements 34.1, 34.2, 34.3, 34.4 change an inclination in respect of the direction of the basic magnetic field 18 and/or the dominant component of the basic magnetic field 18 of the basic magnet 17 by at least 10° up to a maximum of 20°. The two rotatably mounted coil elements 34.1, 34.2, 34.3, 34.4 arranged on a coil axis 35 also have a different working area of rotation in respect of the basic magnetic field 18 and/or the dominant component of the basic magnetic field 18 of the basic magnet 17 in order to thus prevent reciprocal obstruction when a rotary movement is performed.

Figure 5:
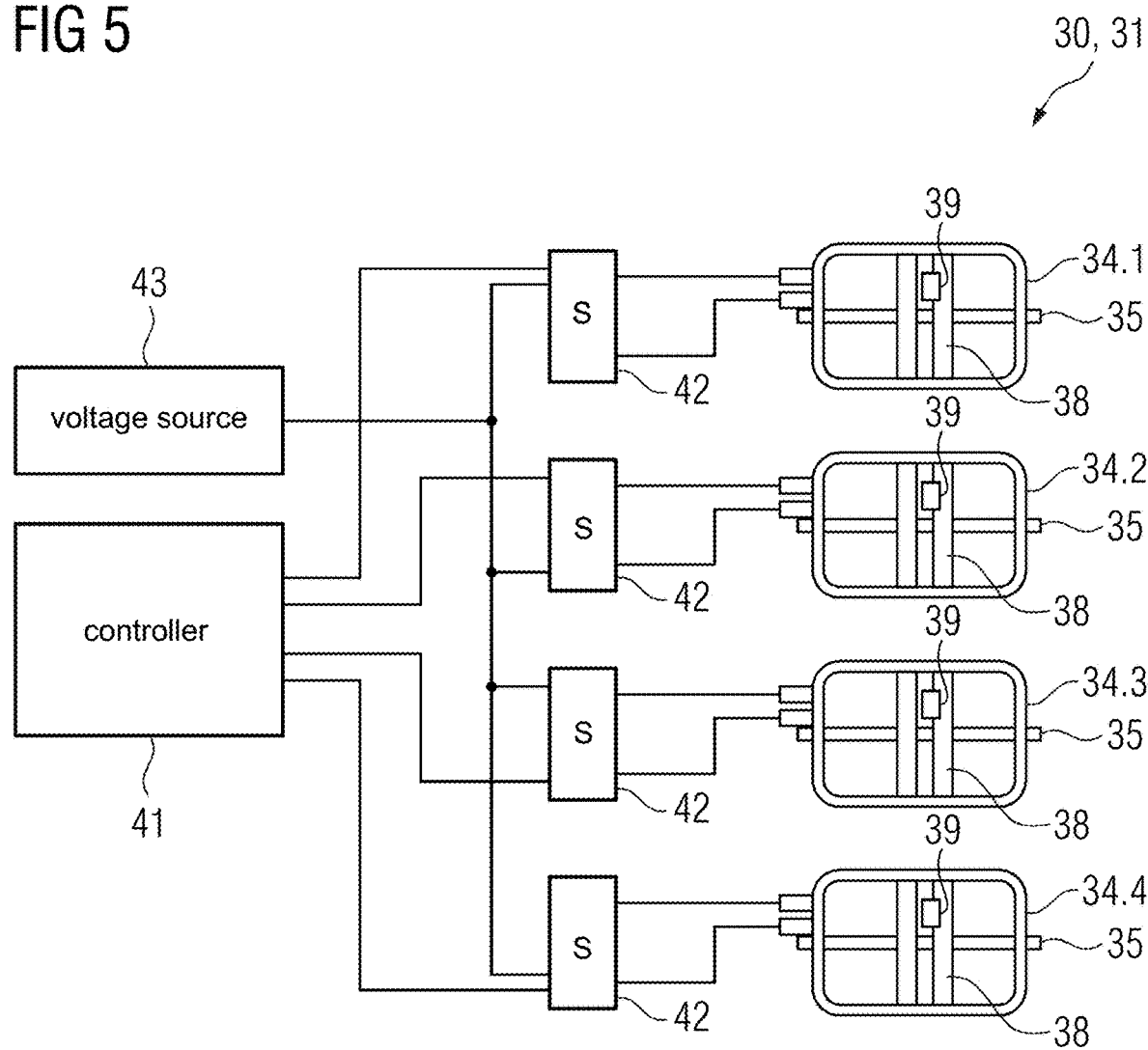
FIG. 5 shows an actuation of the magnetic resonance-compatible drive, according to an exemplary embodiment.

For actuation of the individual rotatably mounted coil elements 34.1, 34.2, 34.3, 34.4 the magnetic resonance-compatible drive 30, in particular the electric step motor, has a controller (FIG. 5). The controller 41 is configured to implement an actuation of the individual rotatably mounted coil elements 34.1, 34.2, 34.3, 34.4 one after the other. In particular, the controller 41 is configured to control a clocking of the individual rotatably mounted coil elements 34.1, 34.2, 34.3, 34.4. The controller 41 can have control software, which is stored in a memory (not shown in further detail) of the controller 41. The individual rotatably mounted coil elements 34.1, 34.2, 34.3, 34.4 can be actuated by means of the control software, which can be executed by a processor and/or an arithmetic module of the controller 41.

For actuation of the individual rotatably mounted coil elements 34.1, 34.2, 34.3, 34.4 the magnetic resonance-compatible drive 30, in particular the electric step motor, also has in each case at least one switching element 42, in particular an electronic switching element 42 (FIG. 5). The individual electronic switching elements 42 are formed in the present exemplary embodiment by one bridge circuit, called an H-bridge, respectively. The bridge circuit, in particular the H-bridge, can comprise a plurality of transistors, in particular bipolar transistors and/or field effect transistors and/or IGBT transistors. In the present exemplary embodiment the magnetic resonance-compatible drive 30, in particular the electric step motor, has exactly one electronic switching element 42, in particular an H-bridge, for each of the rotatably mounted coil elements 34.1, 34.2, 34.3, 34.4. A simple change in a direction of a current flowing through the rotatably mounted coil elements 34.1, 34.2, 34.3, 34.4 can be achieved by means of the H-bridges. For this, the H-bridges are arranged between a voltage supply (voltage source) 43 and the individual rotatably mounted coil elements 34.1, 34.2, 34.3, 34.4. The individual H-bridges are actuated by the controller 41 here.

The individual rotatably mounted coil elements 34.1, 34.2, 34.3, 34.4 are actuated by the controller 41 in such a way that the four coil elements 34.1, 34.2, 34.3, 34.4 each perform a rotary movement one after the other and together bring about a step of the drive shaft 36. In an exemplary embodiment, a step of the drive shaft 36 comprises, in particular, a spacing between two teeth of a toothing of the toothed wheel 37 of the drive shaft 36. A step of this kind can comprise, for example, a rotation of the toothed wheel 37 mounted on the drive shaft 36 and/or a rotation of the drive shaft 36 by 2°. Each of the individual rotatably mounted coil elements 34.1, 34.2, 34.3, 34.4 performs a clock, therefore, which comprises a ¼-step of the toothed wheel 37 mounted on the drive shaft 36. FIGS. 6a-6e show a sequence of the individual clocks for a step of the toothed wheel 37 mounted on the drive shaft 36.

FIG. 6a firstly shows an origin and/or starting point in which the rotatably mounted coil element 34.1, in particular the pinion 38 of the rotatably mounted coil element 34.1, meshes with the toothed wheel 37 of the drive shaft 36. In this starting point only the rotatably mounted coil element 34.1, in particular the pinion 38 of the rotatably mounted coil element 34.1, meshes with the toothed wheel 37 of the drive shaft 36. The three further rotatably mounted coil elements 34.2, 34.3, 34.4, in particular the pinions 38 of the three rotatably mounted coil elements 34.2, 34.3, 34.4, are in a starting position here in which the pinions 38 do not mesh with the toothed wheel 37 of the drive shaft 36.

In addition, FIGS. 6a-6e show the toothed wheel 37 of the drive shaft 36 schematically in a cut-open state. The black point on the toothed wheel 37 indicates the progress with which the toothed wheel 37 moves if the individual rotatably mounted coil elements 34.1, 34.2, 34.3, 34.4, in particular the pinions 38 of the individual rotatably mounted coil elements 34,1 34.2, 34.3, 34.4, mesh one after the other with the toothed wheel 37 of the drive shaft 36 and bring about a rotation of the toothed wheel 37. The black point underneath indicates the starting point, wherein in FIG. 6a the point indicating the progress matches the starting point. The pinions 38 of the individual rotatably mounted coil elements 34.1, 34.2, 34.3, 34.4 mesh with the toothed wheel 37 of the drive shaft 36 if the rotatably mounted coil elements 34.1, 34.2, 34.3, 34.4 abut and/or have arrived at one of the two stop elements 40.

FIG. 6b shows a first clock of the magnetic resonance-compatible drive 30, in particular of the electric step motor. In this first clock, the rotatably mounted coil element 34.2 has performed a rotary movement up to the stop element 40 and triggered a ¼-step of the toothed wheel 37 and/or the drive shaft 26 to the right in the process. The point indicating the progress is removed by ¼-step from the starting point, therefore. In this clock, the rotatably mounted coil element 34.1 is at its starting point again, in other words without meshing of the rotatably mounted coil element 34.1, in particular of the pinion 38 of the rotatably mounted coil element 34.1, with the toothed wheel 37 of the drive shaft 36. In addition, the two further rotatably mounted coil elements 34.3, 34.4, in particular the pinions 38 of the two further rotatably mounted coil elements 34.3, 34.4, are also in a starting position in which there is no meshing with the toothed wheel 37 of the drive shaft 36.

FIG. 6c shows a second clock of the magnetic resonance-compatible drive 30, in particular of the electric step motor. In this second clock, the rotatably mounted coil element 34.3 has performed a rotary movement up to the stop element 40 and initiated a ¼-step of the toothed wheel 37 and/or the drive shaft 36 to the right in the process. The point indicating the progress is a further ¼-step removed from the starting point, therefore. Overall, a spacing between the starting point and the point indicating the progress is accordingly equal to a ½-step. In this clock, the rotatably mounted coil element 34.2 is at its starting point again, in other words without meshing of the rotatably mounted coil element 34.2, in particular of the pinion 38 of the rotatably mounted coil element 34.2, with the toothed wheel 37 of the drive shaft 36. In addition, the two further rotatably mounted coil elements 34.1, 34.4, in particular the pinions 38 of the two further rotatably mounted coil elements 34.1, 34.4, are also in a starting position in which there is no meshing with the toothed wheel 37 of the drive shaft 36.

FIG. 6d shows a third clock of the magnetic resonance-compatible drive 30, in particular of the electric step motor. In this third clock, the rotatably mounted coil element 34.4 has performed a rotary movement up to the stop element 40 and initiated a ¼-step of the toothed wheel 37 and/or the drive shaft 36 to the right in the process. The point indicating the progress is removed a further ¼-step from the starting point, therefore. Overall a spacing between the starting point and the point indicating the progress is accordingly equal to a ¾-step. In this clock, the rotatably mounted coil element 34.3 is at its starting point again, in other words without meshing of the rotatably mounted coil element 34.3, in particular of the pinion 38 of the rotatably mounted coil element 34.3, with the toothed wheel 37 of the drive shaft 36. In addition, the two further rotatably mounted coil elements 34.1, 34.2, in particular the pinions 38 of the two further rotatably mounted coil elements 34.1, 34.2, are in a starting position in which there is no meshing with the toothed wheel 37 of the drive shaft 36.

FIG. 6e shows a fourth clock of the magnetic resonance-compatible drive 30, in particular of the electric step motor. In this fourth clock, the rotatably mounted coil element 34.1 has performed a rotary movement up to the stop element 40 and initiated a ¼-step of the toothed wheel 37 and/or the drive shaft 36 to the right in the process. The point indicating the progress is removed a further ¼-step from the starting point, therefore. Overall, a spacing between the starting point and the point indicating the progress is accordingly equal to a whole step, therefore. In this clock, the rotatably mounted coil element 34.4 is at its starting point again, in other words without meshing of the rotatably mounted coil element 34.4, in particular of the pinion 38 of the rotatably mounted coil element 34.4, with the toothed wheel 37 of the drive shaft 36. In addition, the two further rotatably mounted coil elements 34.2, 34.3, in particular the pinions 38 of the two further rotatably mounted coil elements 34.2, 34.3, are in a starting position in which there is no meshing with the toothed wheel 37 of the drive shaft 36.

The actuation of the individual rotatably mounted coil elements 34.1, 34.2, 34.3, 34.4 by means of the controller 41 for a movement to the right of the toothed wheel 37 of the drive shaft 36 occurs in the order 34.2, 34.3, 34.4, 34.1, therefore. An actuation of the individual rotatably mounted coil element 34.1, 34.2, 34.3, 34.4 by means of the controller 41 for a movement to the left of the toothed wheel 37 of drive shaft 36 occurs in the order 34.4, 34.3, 34.2, 34.1, therefore.

Figure 7:
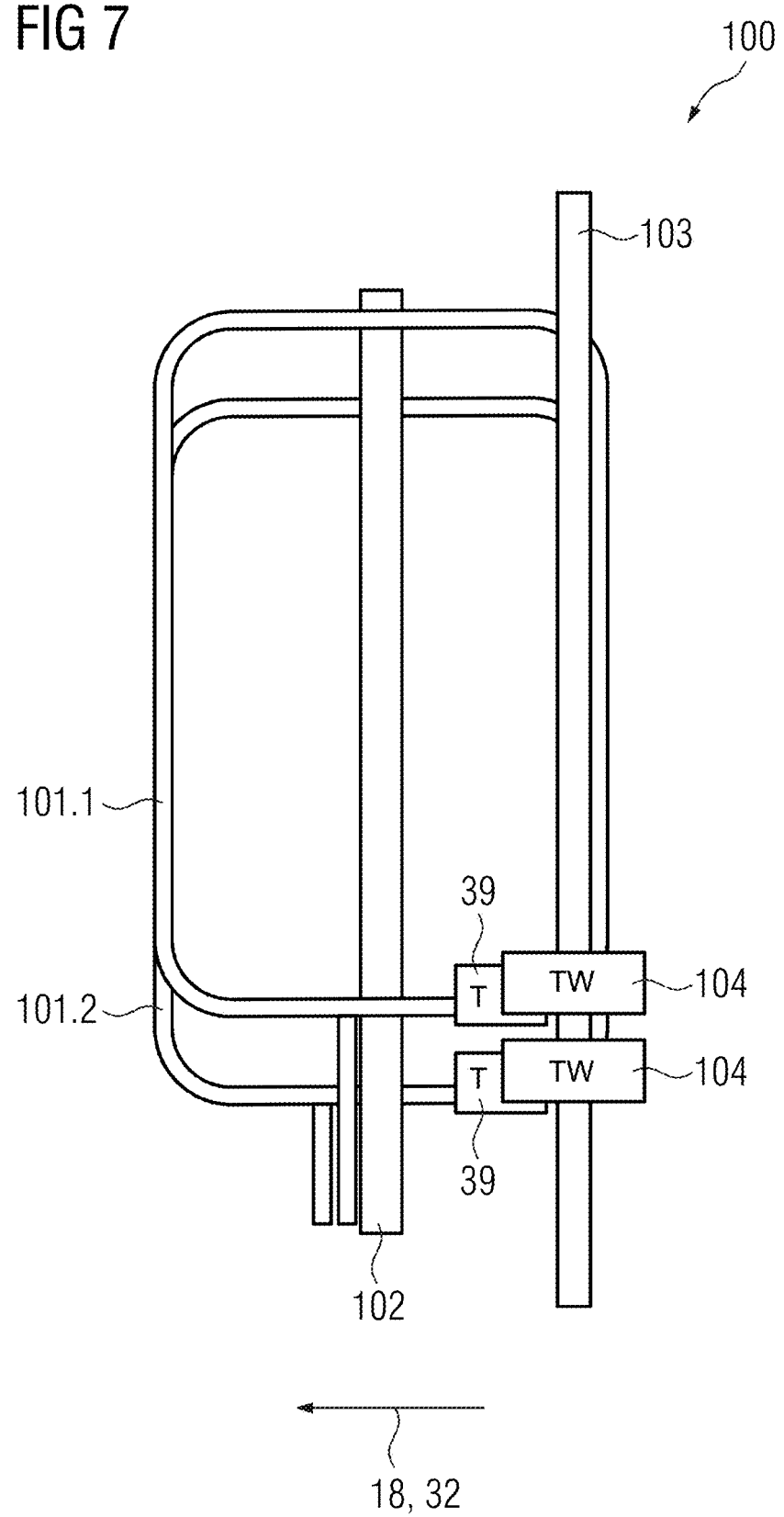
FIG. 7 shows an alternative construction of a magnetic resonance-compatible drive according to an exemplary embodiment.

FIG. 7 shows an alternative exemplary embodiment of the magnetic resonance-compatible drive 100. Components, features and functions that substantially remain the same are basically provided with identical reference characters. The following description is substantially limited to the differences from the exemplary embodiment in FIGS. 2 to 6e, with reference being made to the description of the exemplary embodiment in FIGS. 2 to 6e in respect of components, features and functions that remain the same.

FIG. 7 shows a particularly compact construction of the magnetic resonance-compatible drive 100, in particular of the electric step motor. The magnetic resonance-compatible drive 100, in particular the electric step motor, shown in FIG. 7 also has four rotatably mounted coil elements 101.1, 101.2 (with only two of the four rotatably mounted coil elements 101.1, 101.2 being shown in FIG. 7 for the sake of clarity). In addition, the magnetic resonance-compatible drive 100 has a single coil axis 102 on which all four rotatably mounted coil elements 101.1, 101.2 are mounted. For transfer of a drive moment to the drive shaft 103 of the magnetic resonance-compatible drive 100 the drive shaft 103 has four positive-fitting transfer elements, with the positive-fitting transfer elements each being formed by a toothed wheel 104. Each toothed wheel 104 of the drive shaft 103 is configured for transfer of a drive moment from exactly one of the rotatably mounted coil elements 101.1, 101.2.

In order to prevent obstruction between the individual rotatably mounted coil elements 101.1, 101.2 the individual rotatably mounted coil elements 101.1, 101.2 are arranged mutually offset on the coil axis 102. In the present exemplary embodiment, the individual rotatably mounted coil elements 101.1, 101.2 are arranged mutually shifted and/or offset by the factor (number of the coil element)*4 mm. Thus for example the second rotatably mounted coil element 101.2 is arranged shifted and/or offset by 8 mm in respect of the first rotatably mounted coil element 101.1.

In addition, in a further embodiment of the disclosure, it may also be that individual rotatably mounted coil elements 101.1, 101.2 have coil surfaces of different sizes. In this way a rotatably mounted coil element 101.1, 101.2 can be arranged inside a coil surface of a further rotatably mounted coil element 101.1, 101.2. In order to obtain a substantially constant torque and/or drive moment, however, which is generated by the individual rotatably mounted coil elements 101.1, 101.2, the number of coil windings and/or a strength of a current through the individual rotatably mounted coil elements 101.1, 101.2 have to be aligned with each other for the individual rotatably mounted coil elements 101.1, 101.2.

Generation of a drive moment, and therewith actuation of the individual rotatably mounted coil elements 101.1, 101.2, occurs according to the description relating to FIGS. 5 to 6*e*.

Although the disclosure has been illustrated and described in detail by the preferred exemplary embodiment it is not limited by the disclosed examples and a person skilled in the art can derive other variations herefrom without departing from the scope of the disclosure.

To enable those skilled in the art to better understand the solution of the present disclosure, the technical solution in the embodiments of the present disclosure is described clearly and completely below in conjunction with the drawings in the embodiments of the present disclosure. Obviously, the embodiments described are only some, not all, of the embodiments of the present disclosure. All other embodiments obtained by those skilled in the art on the basis of the embodiments in the present disclosure without any creative effort should fall within the scope of protection of the present disclosure.

It should be noted that the terms "first", "second", etc. in the description, claims and abovementioned drawings of the present disclosure are used to distinguish between similar objects, but not necessarily used to describe a specific order or sequence. It should be understood that data used in this way can be interchanged as appropriate so that the embodiments of the present disclosure described here can be implemented in an order other than those shown or described here. In addition, the terms "comprise" and "have" and any variants thereof are intended to cover non-exclusive inclusion. For example, a process, method, system, product or equipment comprising a series of steps or modules or units is not necessarily limited to those steps or modules or units which are clearly listed, but may comprise other steps or modules or units which are not clearly listed or are intrinsic to such processes, methods, products or equipment.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general-purpose computer.

For the purposes of this discussion, the term "processing circuitry" shall be understood to be circuit(s) or processor(s), or a combination thereof. A circuit includes an analog circuit, a digital circuit, data processing circuit, other structural electronic hardware, or a combination thereof. A processor includes a microprocessor, a digital signal processor (DSP), central processor (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein. In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

The invention claimed is:

1. A magnetic resonance (MR) system comprising:
   a MR device including a scanner with a basic magnet configured to generate a homogeneous basic magnetic field; and
   a magnetic resonance-compatible drive including:
      an electric motor with a stator, and
      two more rotatably mounted coils, wherein:
   the stator of the electric motor comprises a dominant component of the basic magnetic field of the basic magnet; and
   at least two of the two or more rotatably mounted coils are rotatably mounted, independently of each other, on a shared coil axis.

2. The magnetic resonance system as claimed in claim 1, wherein the magnetic resonance-compatible drive comprises a rotatable motor element with at least one rotatably mounted coil and a coil axis oriented perpendicular to the dominant component of the basic magnetic field of the basic magnet, the at least one rotatably mounted coil being rotatably mounted around the coil axis oriented perpendicular to the dominant component of the basic magnetic field of the basic magnet.

3. The magnetic resonance system as claimed in claim 2, wherein, for generation of a drive moment, the at least one rotatably mounted coil is configured to perform a rotary movement that includes a rotation of the at least one rotatably mounted coil by at least 5° up to a maximum of 90° about the coil axis.

4. The magnetic resonance system as claimed in claim 2, wherein, a rotary movement is triggered at the at least one rotatably mounted coil in response to an application of a voltage to the at least one rotatably mounted coil.

5. The magnetic resonance system as claimed in claim 2, wherein the magnetic resonance-compatible drive has at least one stop.

6. The magnetic resonance system as claimed in claim 2, wherein the at least one rotatably mounted coil has a positive-fitting transfer element configured to transfer a drive moment to a drive shaft of the electric motor.

7. The magnetic resonance system as claimed in claim 6, wherein the positive-fitting transfer element comprises a pinion.

8. The magnetic resonance system as claimed in claim 2, wherein the magnetic resonance-compatible drive includes a controller configured to actuate the at least one rotatably mounted coil.

9. The magnetic resonance system as claimed in claim 8, wherein the magnetic resonance-compatible drive includes at least one switch, the actuation of the at least one rotatably mounted coil using the at least one switch.

10. The magnetic resonance system as claimed in claim 1, wherein the magnetic resonance-compatible drive has two or more rotatably mounted coils.

11. The magnetic resonance system as claimed in claim 10, wherein the two or more rotatably mounted coils are configured to be actuated one after the other to cause a rotary movement of the two or more rotatably mounted coils, the two or more rotatably mounted coils being configured such that the rotary movement of the two or more more rotatably mounted coils causes a rotary movement of a drive shaft of the electric motor.

12. The magnetic resonance system as claimed in claim 11, wherein the actuation of the two or more rotatably mounted coils one after the other is configured to perform four clocks of the electric motor, each of the clocks including a ¼-step rotation of the drive shaft to produce a 4-time clock of the electric motor.

13. A magnetic resonance (MR) system comprising:
a MR device including a scanner with a basic magnet configured to generate a homogeneous basic magnetic field; and
a magnetic resonance-compatible drive including: an electric motor with a stator, and two or more rotatably mounted coils, the stator of the electric motor including a dominant component of the basic magnetic field of the basic magnet, wherein the two or more rotatably mounted coils are configured to be actuated one after the other to cause a rotary movement of the two or more rotatably mounted coils, the two or more rotatably mounted coils being configured such that the rotary movement of the two or more rotatably mounted coils causes a rotary movement of a drive shaft of the electric motor.

14. The magnetic resonance system as claimed in claim 13, wherein the actuation of the two or more rotatably mounted coils one after the other is configured to perform four clocks of the electric motor, each of the clocks including a ¼-step rotation of the drive shaft to produce a 4-time clock of the electric motor.

15. The magnetic resonance system as claimed in claim 13, wherein the rotary movement of the drive shaft of the electric motor provides a 4-time clock of the electric motor.

16. The magnetic resonance system as claimed in claim 13, wherein the two or more rotatably mounted coils are configured to rotate independent of each other.

17. The magnetic resonance system as claimed in claim 13, wherein at least two of the two or more rotatably mounted coils are rotatably mounted, independently of each other, on a shared coil axis.

* * * * *